United States Patent
Gobbi Frattini

(10) Patent No.: US 10,945,881 B1
(45) Date of Patent: Mar. 16, 2021

(54) PLURAL-USE DROP-BY-DROP DISPENSER FOR STERILE LIQUID PRODUCT, PARTICULARLY FOR COLLYRIUM OR OTHER MEDICINAL PRODUCT OR MEDICAL DEVICE

(71) Applicant: PAOLO GOBBI FRATTINI S.R.L., Milan (IT)

(72) Inventor: Paolo Giuseppe Gobbi Frattini, Sondalo (IT)

(73) Assignee: PAOLO GOBBI FRATTINI S.R.L., Milan (IT)

( * ) Notice: Subject to any disclaimer, the term of this patent is extended or adjusted under 35 U.S.C. 154(b) by 0 days.

(21) Appl. No.: 16/720,094

(22) Filed: Dec. 19, 2019

(51) Int. Cl.
*A61F 9/00* (2006.01)
*A61J 1/14* (2006.01)
*A61J 1/20* (2006.01)

(52) U.S. Cl.
CPC ........... *A61F 9/0008* (2013.01); *A61J 1/1412* (2013.01); *A61J 1/1456* (2015.05); *A61J 1/2037* (2015.05)

(58) Field of Classification Search
CPC ..... A61F 9/0008; A61J 1/2037; A61J 1/1456; A61J 1/1412
USPC ........................................................ 222/422
See application file for complete search history.

(56) References Cited

U.S. PATENT DOCUMENTS

| | | | | |
|---|---|---|---|---|
| 5,310,094 A | * | 5/1994 | Martinez | B05B 11/0075 222/212 |
| 5,373,972 A | * | 12/1994 | Bystrom | B05B 11/047 222/212 |
| 7,832,594 B2 | * | 11/2010 | Yamada | B65D 1/095 222/189.06 |
| 2002/0193777 A1 | * | 12/2002 | Aneas | A61J 1/2096 604/411 |
| 2004/0074925 A1 | * | 4/2004 | Faurie | A61F 9/0008 222/212 |

FOREIGN PATENT DOCUMENTS

| | | |
|---|---|---|
| EP | 1266840 | 12/2002 |
| IT | 102018000009269 | * 9/2020 |
| UA | 20161615 | 9/2017 |
| WO | WO 9310015 | 5/1993 |

OTHER PUBLICATIONS

Italian Search Report dated Jul. 12, 2019.

* cited by examiner

*Primary Examiner* — Jeremy Carroll
(74) *Attorney, Agent, or Firm* — Jacobson Holman PLLC

(57) ABSTRACT

A plural-use drop-by-drop dispenser for sterile liquid product comprises a vial (1) for containment of the liquid product (2) and a connector (4) provided with a plug (8) which is normally hermetically closed and with a cartridge (19) with sterilizing filter (24) which can be axially moved to force open said plug (8) to dispense the liquid product and allow the hermetic reclosure thereof at the end of dispensing. The cartridge (19) is provided with a filter-holding bottom element (25) provided with a dispensing spout (26), possibly in antimicrobic material, with elastically flexible converging lips (27), which open under pressure of the liquid product (2) for drop-by-drop dispensing thereof and elastically hermetically reclose at the end of the dispensing operation.

5 Claims, 3 Drawing Sheets

PLURAL-USE DROP-BY-DROP DISPENSER FOR STERILE LIQUID PRODUCT, PARTICULARLY FOR COLLYRIUM OR OTHER MEDICINAL PRODUCT OR MEDICAL DEVICE

BACKGROUND OF THE INVENTION

The present invention relates to a plural-use drop-by-drop dispenser for sterile liquid product, particularly for collyrium or other medicinal product or medical device.

Plural-use drop-by-drop dispensers for liquid medicinal products, in particular for collyrium for caring ocular diseases, are very common in the pharmaceutical field.

One of these is for example, described in Italian Patent Application No. 102016000026325 filed on 14 Mar. 2016, and comprises a vial for containment of liquid product, a valve device which is normally hermetically closed by an elastically deformable closing element which can be opened by axial external push for controlled drop-by-drop dispensing of the liquid product contained inside the vial and successively is automatically hermetically reclosable at the stop of said external push, and a cartridge with tubular tang and sterilizing filter which can be handled so that the aforesaid tubular tang can be pushed from outside against said elastically deformable element for its opening for drop-by-drop dispensing of the liquid product and can be successively extracted from said elastically deformable element for its hermetic reclosure at the end of dispensing.

The main problem of this known dispenser consists of the fact that once dispensing has terminated, a small residue of product may remain outside the filter, which may be contaminated by the outside air and in turn contaminate the medicinal product at the successive dispensing. The same outside air may be a source of contamination also in the absence of residue of medicinal product.

SUMMARY OF THE INVENTION

It is the object of the present invention to make a dispenser of the aforesaid type which does not have the above-mentioned problem.

According to the invention, such an object is achieved with a plural-use drop-by-drop dispenser for sterile liquid product, particularly for medicinal product, even more specifically for dispensing collyrium, comprising a vial for containment of the liquid product and a connector provided with a valve device which is normally hermetically closed by an elastically deformable closing element which can be opened by axial external push for controlled drop-by-drop dispensing of the liquid product contained inside the vial and is successively automatically hermetically reclosable at the stop of said external push, and a cartridge with tubular tang and sterilizing filter which can be handled so that the aforesaid tubular tang can be pushed from the outside against said elastically deformable element for its opening for drop-by-drop dispensing of the liquid product and can be successively extracted from said elastically deformable element for its hermetic reclosure at the end of dispensing, characterized in that said cartridge is provided with an end filter-holding bottom element provided with a drop-by-drop dispensing spout, possibly in antimicrobic material, with elastically flexible converging lips, which open under pressure of the liquid product during dispensing operation and elastically hermetically reclose at the end of the dispensing operation.

A removable protecting cover, possibly in antimicrobic material, completely covers the end bottom element of the filter and the aforesaid dispensing spout, thus keeping the two lips of the spout tightly closed between one dispensing operation and the other.

The converging lips of the dispensing spout in essence form a check valve which keeps the area downstream of the cartridge filter sterile and simultaneously prevents the return of liquid residues and/or air therein, thus avoiding any possibility of contamination of the product at the successive dispensing operation.

BRIEF DESCRIPTION OF THE DRAWINGS

A preferred embodiment of the dispenser according to the invention is now described by way of non-limiting example with reference to the accompanying drawings, in which.

DETAILED DESCRIPTION OF THE INVENTION

Figure 1:
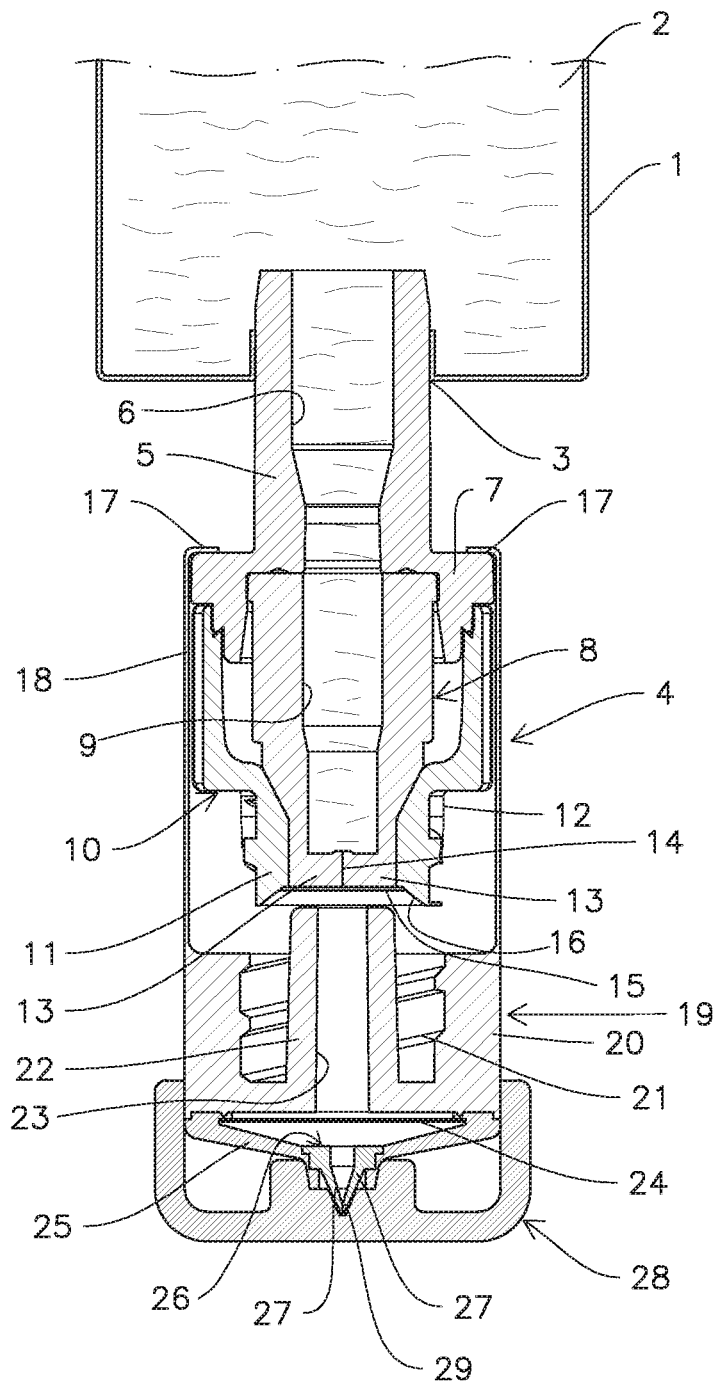
FIG. 1 shows a dispenser according to the invention, in closed condition between one dispensing operation and the successive, with protecting cover applied.

A vial for containment of a medicinal liquid product is indicated in FIG. 1 with 1, the medicinal liquid product being e.g. collyrium, which in turn in indicated with 2. Vial 1 preferably is made in flexible material so as to allow the user to exert pressure to push the liquid product towards an outlet mouth 3 of the vial.

A connector 4 is forced and blocked in mouth 3, the connector comprising a main body 5 containing an axial bore 6, a widened collar 7 and a valve device consisting of a closure plug 8 in elastically deformable plastic material, which in turn has an axial bore 9 arranged to extend bore 6. The closing plug 8 is abutted against the base of collar 7 and is kept in such a position by a ring nut 10 screwed to collar 7. The ring nut 10 has an elastically deformable narrow end mouth 11 provided with external threading 12.

The closing plug 8 ends at the bottom with a pair of elastically flexible lips 13 separated by a thin axial slit 14 having rectangular section, which ends immediately before the lower extremity of plug 8.

A thin elastic sealing membrane 15 formed in one piece with plug 8 is arranged immediately below the two flexible lips 13, at the beginning of a conical flaring 16 of the end mouth 11 of the ring nut 10.

The structural features of membrane 15 are those described in EP 2 667 839 B1, to which explicit descriptive reference is made herein.

Two folds 17 of an axial extension 18 of a filter-holding cartridge 19, which is axially slidable with respect to connector 4, and rests on collar 7. Cartridge 19 is formed by an external body 20 provided with an internal threading 21 compatible for screw coupling with the external threading 12 of the end mouth 11 of the ring nut 10.

An internal tubular tang 22 with axial bore 23, which projects upwards with respect to the external body 20, extends from the base of the external body 20 of cartridge 19.

A sterilizing filter 24 carried by a cup-shaped end bottom element 25 hooked to the base of body 20 is positioned below the body 20 of cartridge 19.

The bottom element 25 is provided with a dispensing spout 26, possibly in antimicrobic material, which has elastically flexible converging lips 27, which are normally hermetically closed, which are capable of opening under pressure of the liquid product for dispensing successive drops of the liquid product 2 and of elastically hermetically reclosing at the end of the dispensing operation.

A removable protecting cover 28, possibly in antimicrobic material, completely covers the end bottom element 25 of cartridge 19 and the aforesaid dispensing spout 26. A conical recess 29 thereof houses the two lips 27 of spout 26, keeping them tightly closed between one dispensing operation and the other.

Figure 2:
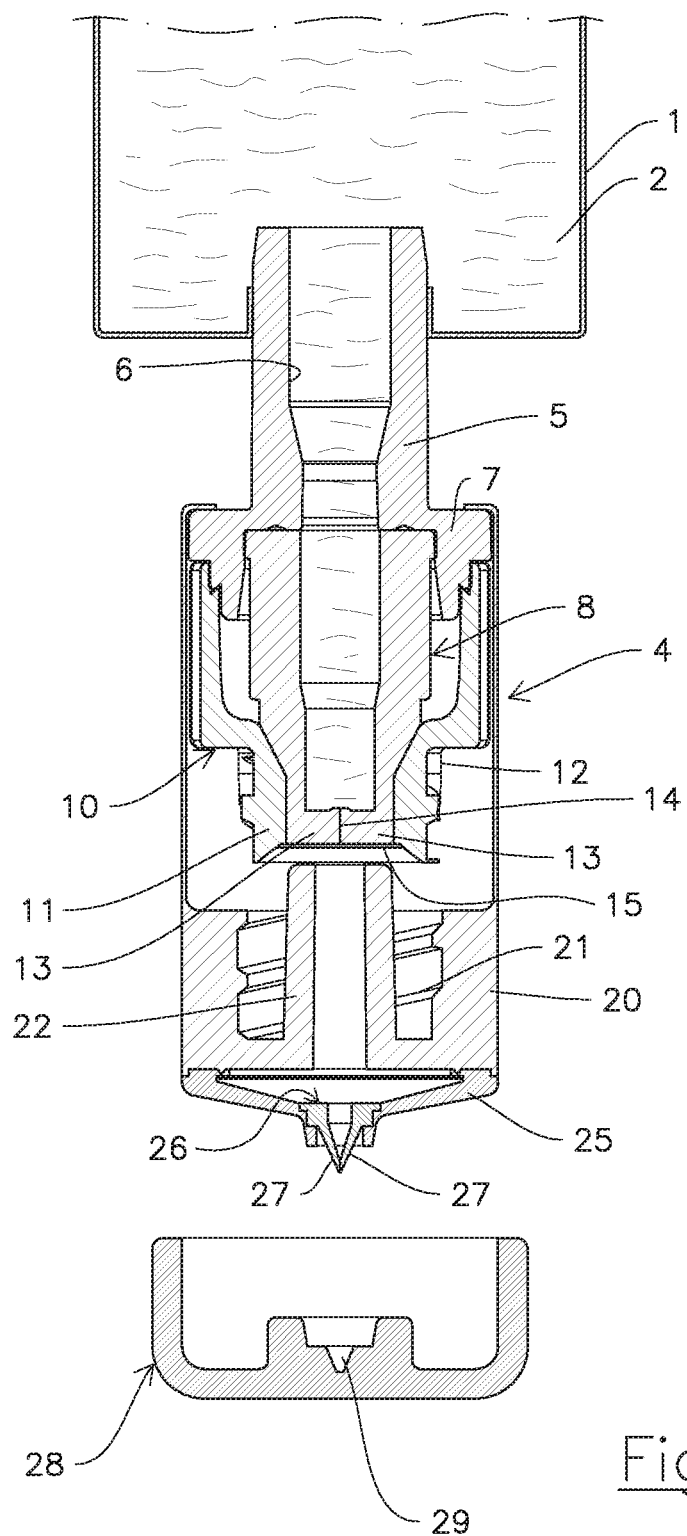
FIG. 2 shows the same dispenser, again in closed position, but with protecting cover removed.

In order to proceed with dispensing a desired number of drops of the liquid product 2, firstly there is a need to remove cover 28, as shown in FIG. 2.

Figure 3:
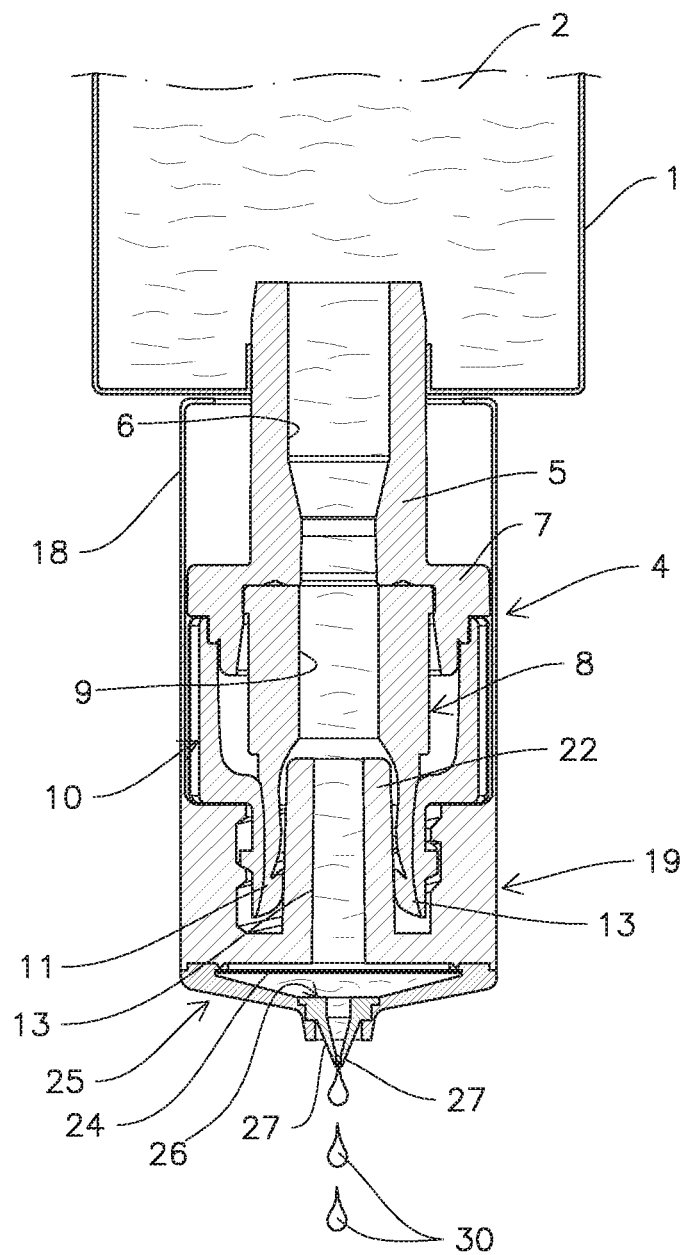
FIG. 3 shows the same dispenser in dispensing operation of the liquid product.

Successively, cartridge 19 is raised and screwed onto the end mouth 11 of the ring nut 10. By doing this, the internal tang 22 of cartridge 19 is push inserted into plug 8, thus first generating the temporary break of membrane 15, and then the temporary moving away of the flexible lips 13 with subsequent widening of slit 14 and the aligned holes 6, 9 and 23 being put into communication, as shown in FIG. 3.

Liquid 2, possibly helped by the pressure of the user's hand on the wall of vial 1, may descend along bore 23, pass through filter 24 and finally come out, in the shape of drops 30, from the space created between the flexible lips 27 and spout 26.

Once the desired number of drops is dispensed, the assembly is turned over, with subsequent return of the liquid product into vial 1 and automatic hermetic reclosure of the lips 27 of spout 26, and cartridge 19 is unscrewed and moved away from the closure plug 8, thus allowing the hermetic reclosure of the flexible lips 13 and of membrane 15. No contamination from the outside is now possible due to the hermetic closure ensured by spout 26.

Finally, the protecting cover 28 is applied again and the assembly is now ready for future dispensing operations in complete safety.

The invention claimed is:

1. A plural-use drop-by-drop dispenser for sterile liquid products, comprising a vial for containment of the liquid product and a connector provided with a valve device which is normally hermetically closed by an elastically deformable closing element which can be opened by axial external push for controlled drop-by-drop dispensing of the liquid product contained inside the vial and is successively automatically hermetically reclosable when said external push is stopped, and a cartridge with a tubular tang and sterilizing filter which, when said tubular tang is pushed from outside against said elastically deformable element for its opening for drop-by-drop dispensing of the liquid product and can be successively extracted from said elastically deformable element for its hermetic reclosure at the end of dispensing, wherein said cartridge is provided with an end filter-holding bottom element provided with a drop-by-drop dispensing spout, with elastically flexible converging lips, which open under pressure of the liquid product during the dispensing operation and automatically elastically hermetically reclose at the end of the dispensing operation.

2. The dispenser to claim 1, wherein said cartridge comprises an external body, which is axially slidable and screwable on a part of said connector, and said tubular tang extends inside said external body and projects axially therefrom and towards said connector so that axial sliding and screwing of the cartridge on said part of the connector causes opening of said elastically deformable element by axial push from said tang.

3. The dispenser according to claim 2, wherein said valve device is formed by a closure plug of the connector which is passed through by an axial bore, and said elastically deformable element is placed to close said axial bore and comprises a pair of elastically flexible lips, which are normally closed to define a thin slit between them and an elastic sealing membrane placed to close said slit and are openable together with said flexible lips by push of said tubular tang of the cartridge, said flexible lips and said membrane being automatically reclosable to hermetic condition upon extraction of said tubular tang.

4. The dispenser according to claim 1, wherein comprising a removable protecting cover placed to cover said end bottom element of the cartridge and of said drop-by-drop dispensing spout.

5. The dispenser according to claim 1, wherein a said protecting cover is provided with a conical recess intended to accommodate and press together said flexible lips of the spout when said protecting cover is applied to cover said bottom element and said spout.

* * * * *